United States Patent

Chaykin

[11] Patent Number: 5,843,471
[45] Date of Patent: Dec. 1, 1998

[54] ORAL CLEANSING: METHODS AND COMPOSITIONS

[76] Inventor: Sterling Chaykin, 1027 Maple La., Davis, Calif. 95616

[21] Appl. No.: 965,344

[22] Filed: Nov. 6, 1997

[51] Int. Cl.⁶ .............................. A61K 7/16; A61K 9/68; A61K 9/20
[52] U.S. Cl. .......................... 424/440; 424/435; 424/49; 426/3; 426/650; 426/660
[58] Field of Search .................................. 424/435, 440, 424/48; 426/69–88, 3, 650, 660

[56] References Cited

U.S. PATENT DOCUMENTS

| | | | |
|---|---|---|---|
| 4,386,106 | 5/1983 | Merritt et al. | 426/5 |
| 4,515,769 | 5/1985 | Merritt et al. | 424/49 |
| 4,632,824 | 12/1986 | Hirota et al. | 424/49 |
| 4,855,128 | 8/1989 | Lynch et al. | 424/49 |
| 5,554,410 | 9/1996 | Bell et al. | 426/660 |

FOREIGN PATENT DOCUMENTS

| | | |
|---|---|---|
| 48006787B | 9/1973 | Japan. |
| 54038180B | 11/1979 | Japan. |
| 58038208A2 | 3/1983 | Japan. |
| 63253018A | 10/1988 | Japan. |
| 06153800A2 | 6/1994 | Japan. |
| 08291013A2 | 11/1996 | Japan. |
| 09327504A2 | 12/1997 | Japan. |

OTHER PUBLICATIONS

Chem Abstr. 67:20755 of Fang–Yung Kalebopek. Konditer 11(4):25–27, 1967.

*Primary Examiner*—Shep K. Rose
*Attorney, Agent, or Firm*—Richard Aron Osman

[57] ABSTRACT

The invention relates to edible oral cleansing and sanitizing compositions and the use of these compositions for reducing plaque and calculus deposition in the mouth and improving oral cleanliness and tooth smoothness. The active ingredients include surfactants, sequestrants, and protein precipitants; each present in a specified concentration range. In a preferred embodiment, the hard candies comprise between about 0.01 and 20% surfactant, especially a glyceride or alkyl sulfate, 0.01 and 10% sequestrant, especially citric acid, and 0.01% and 10% protein precipitant, especially tannic acid.

4 Claims, No Drawings

ORAL CLEANSING: METHODS AND COMPOSITIONS

TECHNICAL FIELD

The field of the invention is ingestible oral cleansing compositions.

BACKGROUND

The removal of food/oral debris, the minimization of the microbial population in the mouth and throat, and the removal and prevention of plaque and calculus deposition are important for the enhancement of personal feelings of well-being (clean breath, mouth taste and mouth feel) and the prevention of oral diseases. Since the oral environment is conducive to microbial growth and subject to the reintroduction of food and microorganisms, and because plaque and calculus are continually being deposited on teeth, ideal oral hygiene methods and compositions must be a) capable of good cleansing and microbial knockdowns, b) able to remove plaque and calculus and prevent their formation, and c) convenient and safe for repetitive use. Traditional mouth washes and dentrifices suffer in all three areas.

The practice of good oral hygiene is especially complicated by the large number of limited scope methods and compositions which seem to be required in order to achieve the overall goal. These are inconvenient because they require a variety of devices, preparations and methods including extensive rubbing, brushing, pushing, flushing, etc. with devices ranging from tooth brushes to tooth picks, floss, gums, effervescent rinses and such. They often imply the availability of water, sinks, tubes, bottles and privacy.

Many current strategies for achieving good oral hygiene tend to thwart rather than foster physiological cleansing and sanitation mechanisms. Most give little or no attention to the back of the oral cavity and upper regions of the throat.

Given the cost in time, money and social awkwardness, most individuals adopt an abbreviated rather than a fall program of oral care. In many cases they are motivated to do less by the realization that whatever they do vis-a-vis personal oral hygiene they cannot escape one or more annual visits to the dental hygienist for painful scaling and polishing. When faced with bad breath or objectionable residual tastes in the mouth and throat, resulting from a build up of food, oral debris, and bacteria, it is not uncommon for individuals to resort to cover-ups having stronger, more acceptable smells or tastes (mint for example) rather than a clean-up. In short, the methods and compositions currently available to the consumer do not permit the typical hygiene conscious individual to maintain a clean, plaque and calculus free mouth without the periodic painful intervention of a dental professional. In particular, what is glaringly absent is a simple inexpensive consumer based strategy which builds on physiological mechanisms existent in the oral cavity and serves to 1) keep the mouth clean between meals and snacks, 2) prevent the deposition of plaque and calculus and 3) remove deposits of plaque and calculus which form during lapses in adherence to the prevention dimension. The present invention represents just such a strategy.

RELEVANT LITERATURE

Numerous references disclose the use of one or more components of the subject compositions, including U.S. Pat. Nos. 4,191,744, 4,849,227, 4,666,708, 5,630,999, 5,120,528, 3,954,962, 5,662,888, 5,514,366, 5,338,538, 4,374,822, 4,107,291, 5,597,562, 5,380,530, 5,320,831, 5,560,905, 5,578,294, 5,620,679, 5,622,689, 5,032,387, 5,143,720 and 5,316,758.

SUMMARY OF THE INVENTION

The present invention relates to edible oral cleansing and sanitizing compositions and the use of these compositions for reducing plaque and calculus deposition in the mouth and improving oral cleanliness and tooth smoothness. The active ingredients include safe and effective amounts of one or more members selected from each of three classes of cleansing and sanitizing agents, namely surfactants, sequestrants (chelators), and protein flocculators (coagulants/denaturants/precipitants), and optionally, one or more stimulators of saliva flow and osmotically active substances capable of plasmolysis of bacteria. In a preferred embodiment, hard candies comprising between about 0.01 and 20% surfactant, especially an alkyl sulfate such as sodium lauryl sulfate, between about 0.01 and 10% sequestrant, especially a polycarboxylic acid such as citric acid, and between about 0.01 and 10% protein flocculent, especially tannic acid are provided. The stimulation of saliva flow being induced either by acidity, provided for example by a polycarboxylic acid, such as citric acid (between 0.1 and 10%), and/or resulting from the masticatory activity implied by a chewing gum vehicle. Accordingly, the requisite active ingredients may be provided by fewer than five separate compounds (i.e. one compound may provide a plurality of active ingredients). For example, citric acid can provide both the sequestrant and the stimulator of salivary flow. Sugars and/or sugar alcohols (between about 60 and 99%) which make up the hard candy or are made part of the chewing gum formulation serve in the osmotic role.

DESCRIPTION OF SPECIFIC EMBODIMENTS

The disclosed compositions comprise a surfactant, a protein flocculator, a sequestrant, and optionally, a stimulator of saliva flow, and an osmotically active substance, which together serve to remove residual tastes from the palate, eliminate food and oral debris, reduce the size of the oral microbial flora, and inhibit plaque and calculus deposition. The compositions may further comprise inactive ingredients. All ingredients may be ingested and preferably are U.S. FDA approved (GRAS) foods or food additives. Given its edible design, the composition permits a bypassing of the equipment requirement of traditional oral sanitizers, such as brushes, floss, sinks, etc. In many formulations here need be no waste disposal issue either; all the user needs to do is swallow. When formulated as a hard candy, this invention can be conveniently used in any social setting (after any meal or snack) to cleanse and sanitize the oral cavity and throat. In contrast to most oral hygiene programs, which tend to be regarded as necessary chore with little or no immediate personal gratification, the clean mouth taste and feel which results from sucking on a hard candy formulated according to this invention is a strong inducement for its use every time an individual eats or drinks anything. The disappearance of old coffee, onion, and garlic tastes and oily films from the oral cavity is startlingly obvious. Users appreciate the substitution of a clean taste, for the typical minty aftertaste of dentifrices and after dinner candies.

The active ingredients are believed to function as follows. Surfactants dislodge food residues, plaque, and bacteria from oral surfaces and bring them into suspension. They also kill bacteria by disrupting their cell membranes and, in the presence of salivary lysozyme, facilitate bacterial cell lysis. Protein precipitants/flocculators denature and/or competitively remove proteins from teeth so they can more easily be brought into suspension, kill bacteria by reacting with bacterial membrane proteins and disrupt plaque and calculus deposition. Sequestrants destabilize the structures of food materials and oral debris, inhibit the calcification of plaque by demineralization (making it more vulnerable to the abrasive actions of brushing and flossing) and kill bacteria by destabilizing bacterial cell membranes through the removal of metal ions. Osmotically active substances facilitate the disruption of bacteria through plasmolysis. The stimulation of saliva flow by gustatory and masticatory signals results in a more fluid saliva, due to the increased proportion of parotid saliva in the salivary mix, increasing solvent action and adding a number of cleansing, sanitation and protection components, including lysozyme, peroxidase, lactoferrin, lectins, immunoglobulins, calcium phosphate (for remineralization), fluoride, etc. Swallowing the resulting suspension effectively cleans the oral cavity.

The subject compositions generally comprise between about 0.01 and 20%, preferably between about 0.05 and 5%, more preferably between about 0.1 and 2% by weight surfactant, or mixtures thereof, depending on the specific surfactant(s) used, including anionic, cationic, nonionic and zwitterionic species. Suitable concentrations are readily determined empirically in consideration of oral tolerance and palatability. Exemplary surfactants include monoglycerides and diglycerides, monoglyceride sulfonates, other fatty acid esters, fatty acids and their water-soluble salts, alkyl sulfates and their salts, polysorbates, alkyl quaternary ammonium compounds, alkyl sulfoacetates and their salts, alkyl polyglycol ether carboxylates, polyoxyethylene and polyoxybutylenes and copolymers, phosphonates, prooxylated cetyl alcohol, etc. Preferred surfactants include sodium alkyl sulfates and sulfoacetates, sodium lauryl sulfate, sodium lauryl sarcosinate, polyetheleneglycol stearate, and monoglyceride sulfonates; more preferred surfactants include sodium lauryl sulfate, sodium lauryl sarcosinate; and most preferred surfactants include sodium lauryl sulfate (SLS).

The subject compositions generally comprise between about 0.01 and 10%, preferably between about 0.05 and 1%, more preferably between about 0.1 and 0.5% by weight protein precipitant (or flocculant or denaturant), or mixtures thereof, depending on the specific protein precipitant(s) used and proportion of other components. Suitable concentrations are readily determined empirically in consideration of oral tolerance and palatability. Preferred precipitants are large polyionic molecules which displace the proteinaceous pellicle from the teeth and form linkages with and among proteins. Preferred precipitants include chondroitin sulfate, protamine sulfate, tannic acid, etc.

The subject compositions generally comprise between about 0.01 and 10%, preferably between about 0.05 and 5%, more preferably between about 0.2 and 2% by weight sequestrant (chelator), or mixtures thereof, depending on the specific sequestrant(s) used and proportion of other components. Suitable concentrations are readily determined empirically in consideration of oral tolerance and palatability. Exemplary sequestrants include polycarboxylic acid and their salts and esters, disodium ethylene diamine tetra acetic acid (disodium EDTA), salts of phosphoric acid and pyrophophoric acid, etc. Preferred sequestrants include citric and tartaric acids.

The subject compositions may also comprise other ingredients of varieties and concentrations commonly found in commercial hard candies, lozenges, gums, etc. These include one or more sweeteners such as sugars, sugar alcohols and artificial sweetners, e.g. sucrose, corn syrup, sorbitol, manitol, sodium cyclamate, saccharine, aspartame, xylitol, etc. Caloric sugar sweeteners are generally are present at between about 30 and 99%, preferably between about 60 and 98% by weight, and more preferably between about 80 and 96% by weight. A wide variety of other compounds may be present so long as they are not incompatible with the intended use of the compositions, e.g. they must be safe for human ingestion in the contemplated quantities, they must be palatable and have no offensive odor or taste, etc. Exemplary additional compounds include a source of fluoride, humectants, preservatives (e.g. sodium benzoate) flavoring agents, gums, extenders, binders and other materials whose purposes are to improve product manufacture, product stability, and palatability. The subject compounds are also at least partially hydrated, i.e. they contain at least about 1%, preferably at least about 2%, more preferably at least about 4% water, though water content is not considered in the concentration-expressed ranges herein.

Although hard candies are the preferred formulation other delivery systems amenable to implementing the edible dimension of this invention are encompassed by it, for example, other candies (soft, lozenges, tablets, etc.) gums (see, e.g. U.S. Pat. No. 5,380,530), liquids (sprays, rinses, beverages, etc.), etc. Hard candies of the invention are typically formulated for a total weight of 1–8 g, preferably 2–4 g.

Without further description, one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. Other generic configurations will be apparent to one skilled in the art. All publications and patent applications cited in this specification are herein incorporated by reference as if each individual publication or patent application were specifically and individually indicated to be incorporated by reference.

EXAMPLES

| Formulation #1 | |
| --- | --- |
| Sucrose | 54% |
| Corn Syrup | 38% |
| Water | 7% |
| Sodium lauryl sulfate | 0.11% |
| Tannic Acid | 0.18% |
| Citric Acid | 0.11% |
| Formulation #2 | |
| Sucrose | 72% |
| Corn Syrup | 26% |
| Water | 1% |
| Sodium lauryl sulfate | 0.16% |
| Tannic Acid | 0.24% |
| Citric Acid | 0.09% |
| Formulation #3 | |
| Sucrose | 55% |
| Corn Syrup | 35% |
| Water | 9% |
| Sodium lauryl sarcosinate | 0.10% |
| Chondroitin sulfate | 0.20% |
| Tartaric Acid | 0.10% |

Formulations were demonstrated to (1) produce subjectively smooth feeling teeth and a clean tasting mouth (2) reduce both preexisting calculus and plaque and the formation of new deposits and (3) result in a 10,000-fold reduction in bacterial flora of the oral cavity (as determined by blood agar cultures).

Demonstration #1

4 g hard candy of either formulation #1 (supra), #2$\Delta_1$, #2$\Delta_2$ or #2$\Delta_3$, was dissolved orally four times daily over 2 weeks. The candies were administered immediately after each of three meals and immediately after a late evening tooth brushing. Formulation #2$\Delta_1$ was identical to formulation #2 except for the omission of sodium lauryl sulfate; formulation #2∆₂ was identical to formulation #2 except for the omission of tannic acid, and; formulation #2∆₃ was identical to formulation #2 except for the omission of citrate.

After two weeks, subjects were evaluated for calculus and plaque reduction (from established pre-treatment baselines) and queried for subject evaluation of improvements in cleanliness of mouth taste and smoothness of tooth feel. Results, summarized below (Table 1) reveal that inclusion of all three active ingredients provide demonstrable reductions in calculus/plaque formation and improvements in perceptions of both oral cleanliness and tooth smoothness. Furthermore, efficacy was compromised by the elimination of any one of the precipitant, sequestrant or surfactant.

TABLE 1

| Treatment Formulation | Calculus/Plaque Reduction | Oral Cleanliness | Tooth Smoothness |
|---|---|---|---|
| #2 | +++++ | +++++ | +++++ |
| #2∆₁ | 0 | 0 | 0 |
| #2∆₂ | 0 | + | 0 |
| #2∆₃ | 0 | ++ | 0 |

Demonstration #2

4 g hard candy of either formulation #3 (supra), #3∆₁, #3∆₂ or #3∆₃, is dissolve orally four times daily over 2 weeks. The candies are administered immediately after each of three meals and immediately after a late evening tooth brushing. Formulation #3∆₁ is identical to formulation #3 except for the omission of sodium lauryl sarcosinate; #3∆₂ is identical to #3 except for the omission of chondroitin sulfate, and; #3∆₃ is identical to #3 except for the omission of tartaric acid.

After two weeks, subjects are evaluated for calculus and plaque reduction (from established pre-treatment baselines) and queried for subject evaluation of improvements in cleanliness of mouth taste and smoothness of tooth feel. Results, summarized below (Table 2) reveal that inclusion of all three active ingredients provide demonstrable reductions in calculus/plaque formation and improvements in perceptions of both oral cleanliness and tooth smoothness. Furthermore, efficacy is compromised by the elimination of any one of the precipitant, sequestrant or surfactant.

TABLE 2

| Treatment Formulation | Calculus/Plaque Reduction | Oral Cleanliness | Tooth Smoothness |
|---|---|---|---|
| #3 | +++++ | +++++ | +++++ |
| #3∆₁ | 0 | 0 | 0 |
| #3∆₂ | 0 | + | 0 |
| #3∆₃ | 0 | ++ | 0 |

While this invention has been described in terms of certain preferred embodiments, it should be understood that these are by way of illustration and the invention is not necessarily limited thereto. It will be recognized by those skilled in the art that many modifications and variations are possible without departing from the scope and spirit of the invention. Accordingly such variations and modifications are considered to be within the purview and scope of the invention and the following claims.

What is claimed is:

1. An edible hard candy composition for reducing plaque and calculus deposition in the mouth and improving oral cleanliness and tooth smoothness, said composition comprising:

a) a safe and effective amount of between about 0.01 and 20% of an ingestible surfactant effective to kill bacteria by disrupting their cell membranes and facilitate bacterial cell lysis in the presence of salivary lysozyme;

b) a safe and effective amount of between about 0.01 and 10% of an ingestible sequestrant;

c) a safe and effective amount of between about 0.01 and 10% of tannic acid;

d) a safe and effective amount of between 0.1 and 10% of a stimulator of salivary flow selected from the group consisting of citric acid and tartaric acid; and e) a safe and effective amount of between about 30 and 99% of an osmotically active caloric sugar sweetener selected from the group consisting of sugar and sugar alcohols which facilitate the disruption of bacteria through plasmolysis, wherein said hard candy composition is at least partly hydrated and formulated for orally administratable plaque and calculus reducing dosage forms of from about 1 to 10 grams.

2. A composition according to claim 1 wherein said surfactant is present at a concentration less than about 5% by weight and said sequestrant and said flocculant are each present at a concentration less than about 1% by weight.

3. A method for reducing plaque and calculus deposition in the mouth and improving oral cleanliness and tooth smoothness; said method comprising introducing into a mouth an edible composition according to claim 1, and dissolving said composition with saliva.

4. A composition according to claim 1, wherein the surfactant is selected from the group consisting of sodium lauryl sulfate and sodium lauryl sarcosinate.

* * * * *